US008927459B2

(12) United States Patent
Howerton et al.

(10) Patent No.: US 8,927,459 B2
(45) Date of Patent: Jan. 6, 2015

(54) VEGETATION TREATMENT (71) Applicant: Arctic, Inc., Clemmons, NC (US)

(72) Inventors: Robby James Howerton, Clemmons, NC (US); Gina Marie Stewart, Clemmons, NC (US); Steven Lee Worm, Raleigh, NC (US)

(73) Assignee: Arctic, Inc., Clemmons, NC (US)

( * ) Notice: Subject to any disclaimer, the term of this patent is extended or adjusted under 35 U.S.C. 154(b) by 0 days.

(21) Appl. No.: 13/791,330

(22) Filed: Mar. 8, 2013

(65) Prior Publication Data
US 2013/0190174 A1 Jul. 25, 2013

Related U.S. Application Data (63) Continuation of application No. 12/814,181, filed on Jun. 11, 2010, now Pat. No. 8,627,596, and a continuation-in-part of application No. 12/499,841, filed on Jul. 9, 2009, now abandoned.

(60) Provisional application No. 61/079,513, filed on Jul. 10, 2008.

(51) Int. Cl.
*A01G 7/02* (2006.01)
*A01N 25/00* (2006.01)
*A01M 21/00* (2006.01)
*A01M 21/04* (2006.01)

(52) U.S. Cl.
CPC ............... *A01G 7/02* (2013.01); *A01M 21/04* (2013.01); *A01N 25/00* (2013.01); *A01M 21/00* (2013.01)
USPC ........ 504/116.1; 504/162; 504/189; 118/715; 118/724; 47/1.43; 435/1.3

(58) Field of Classification Search
USPC ................... 47/1.7, 1.43, 1.44; 118/305, 684; 134/46, 52, 180; 239/165, 176, 288.5, 239/332, 526.7; 504/116.1
See application file for complete search history.

(56) References Cited

U.S. PATENT DOCUMENTS 2,290,942 A 7/1942 Clary et al.
4,199,896 A * 4/1980 Lehman ........................... 47/1.7
(Continued)

FOREIGN PATENT DOCUMENTS

JP 2000106868 4/2000
JP 2000290117 10/2000
WO WO 2010/008286 1/2010

OTHER PUBLICATIONS

Fergedal, "Weed Control by Freezing with Liquid Nitrogen and Carbon Dioxide Snow: A Comparison Between Flaming and Freezing," Jul. 1993; Non Chemical Weed Control, Dijon, France; Communications of the Fourth International Conference I.F.O.A.M., pp. 163-166.*

(Continued)

*Primary Examiner* — Jane C Osweck
(74) *Attorney, Agent, or Firm* — Myers Bigel Sibley & Sajovec, P.A.

(57) ABSTRACT

A method is provided for inhibiting plant growth by inducing hypothermia by applying a treating substance to summer annual weeds and grasses. Susceptible undesirable plants will be killed by this treatment, while non-susceptible desirable plants will not be adversely affected by this treatment. Compressed carbon dioxide may be applied to other summer grasses to cause the grasses to become dormant. An apparatus is provided for inducing hypothermia in undesirable plants by applying a treating substance. A canister capable of housing gas may be provided. A valve may be provided to control the amount and pressure of gas dispensed from the canister.

4 Claims, 4 Drawing Sheets (56) References Cited

U.S. PATENT DOCUMENTS

| | | | |
|---|---|---|---|
| 4,322,910 A * | 4/1982 | Garbo | 47/1.7 |
| 5,972,679 A | 10/1999 | Griffith | |
| 5,972,686 A | 10/1999 | Kang et al. | |
| 6,491,231 B1 | 12/2002 | Eliasson et al. | |
| 6,966,144 B2 * | 11/2005 | Eliasson et al. | 43/132.1 |

OTHER PUBLICATIONS

Patton et al., "Zoysiagrass Species and Genotypes Differ in Their Winter Injury and Freeze Tolerance", 2007, Crop Science, 47:1619-1627.*
Abe et al. "An Ice Nucleation Active Gene of *Erwinia ananas*" *FEBS Letters* 258(2):297-300 (1989).
Anderson et al. "Longer Exposure Durations Increase Freeze Damage to Turf Bermudagrasses" *Crop Science* 43:973-977 (2003).
Brown et al. "Field Study Testing the Efficacy of Cryonite© Against Bed Bugs *Cimex lectularius*" *International Pest Control* 54(4):196-199 (Jul./Aug. 2012).
Cary and Mayland. "Factors Influencing Freezing of Supercooled Water in Tender Plants" *Agronomy Journal* 62:715-719 (1970).
Creech et al. "Purple Deadnettle (*Lamium purpureum*) and Soybean Cyst Nematode Response to Cold Temperature Regimes" *Weed Science* 55:592-598 (2007).
Fergedal. "Weed Control by Freezing with Liquid Nitrogen and Carbon Dioxide Snow: A Comparison Between Flaming and Freezing" *Non Chemical Weed Control*, Dijon (France), Jul. 5-9, 1993; Communications of the Fourth International Conference I.F.O.A.M., pp. 163-166 (1993).
Goodnow et al. "Subacute Inhalation Toxicity Study of an Ice-Nucleation-Active *Pseudomonas syringae* Administered as a Respirable Aerosol to Rats" *Toxicology Letters* 52(2-3):157-167 (1990) (Abstract Only).
Hirano and Upper. "Bacteria in the Leaf Ecosystem with Emphasis on *Pseudomonas syringae*—Pathogen, Ice Nucleus, and Epiphyte" *Microbiology and Molecular Biology Reviews* 64(3):624-653 (2000).
Hwang et al. "Expression of a Bacterial Ice Nucleation Gene in a Yeast *Saccharomyces cervisiae* and its Possible Application in Food Freezing Processes" *J Agric Food Chem* 49:4662-4666 (2001).
International Preliminary Report on Patentability Corresponding to International Application No. PCT/US11/39548; Date of Mailing: Jan. 3, 2013; 9 Pages.
International Search Report and Written Opinion of International Application No. PCT/US2011/039548; mailed Sep. 13, 2011 (13 pages).
Kozloff et al. "Ice Nucleating Activity of *Pseudomonas syringae* and *Erwinia herbicola*" *Journal of Bacteriology* 153(1):222-231 (1983).
Lindow and Upper. "*Erwinia herbicola*: A Bacterial Ice Nucleus Active in Increasing Frost Injury to Corn" *Phytopathology* 68:523-527 (1978).
Lindow et al. "Distribution of Ice Nucleation-Active Bacteria on Plants in Nature" *Applied and Environmental Microbiology* 36(6):831-838 (1978).
Lindow, "The Role of Bacterial Ice Nucleation in Frost Injury to Plants" *Ann Rev Phytopathol* 21:363-384 (1983).
Maki et al. "Ice Nucleation Induced by *Pseudomonas syringae*[1]" *Applied Microbiology* 28(3):456-459 (1974).
McGovern et al. "[Annual Cockroach Control Issue] A Cool Way to Manage Roaches" www.pctonline.com (Jul. 2012) (5 pages).
Miller and Dickens. "Potassium Fertilization Related to Cold Resistance in Bermudagrass" *Crop Science* 36:1290-1295 (1996).
News Article about Jacob Schindler, entitled "Teen Scientist, Inventor Kills Kudzu" written by Dean Poling of *The Valdosta Daily Times*, Valdosta, Georgia, May 24, 2010, (4 pages).
Patton and Reicher. "Zoysiagrass Species and Genotypes Differ in Their Winter Injury and Freeze Tolerance" *Crop Science* 47:1619-1627 (2007).
Pooley and Brown. "Effects of Culture Conditions on Expression of the Ice Nucleation Phenotype of *Pseudomonas syringae*" *FEMS Microbiology Letters* 77:229-232 (1991).
Pouleur et a. "Ice Nucleation Activity in *Fusarium acuminatum* and *Fusarium avenaceum*" *Applied and Environmental Microbiology* 58(9):2960-2964 (1992).
PRWeb "Stern Environmental Group Becomes a North American Sales Representative for the Revolutionary "Green" Cryonite Bed Bug Extermination System from CTS Technologies" Secaucus, NJ (Jun. 20, 2008) (www.prweb.com) (2 pages).
Schimming and Messersmith. "Freezing Resistance of Overwintering Buds of Four Perennial Weeds" *Weed Science* 36:568-573 (1988).
Sterix Inc. "Cryonite Poison-Free Pest Control Now in the Philippines!" (sterix.net/cryonite) Alabang Muntinlupa City, Philippines (2010) (4 pages).
Stoller. "Differential Cold Tolerance of Quackgrass and Johnsongrass Rhizomes" *Weed Science* 25(4):348-351 (1977).
Susko and Hussein. "Factors Affecting Germination and Emergence of Dame's Rocket (*Hesperis matronalis*)" *Weed Science* 56:389-393 (2008).
Upper and Vali, "The Discovery of Bacterial Ice Nucleation and its Role in the Injury of Plants by Frost" Chapter 2 in *Biological Ice Nucleation and Its Applications*, pp. 29-39; eds. Richard E. Lee, Jr., Gareth J. Warren and Lawrence V. Gusta, American Phytopathological Society (1995).
Zhang et al. "Bermudagrass Freezing Tolerance Associated with Abscisic Acid Metabolism and Dehydrin Expression During Cold Acclimation" *J Am Soc Hort Sci* 133(4):542-550 (2008).

* cited by examiner

VEGETATION TREATMENT

STATEMENT OF PRIORITY

This application is a continuation application of, and claims priority to, U.S. application Ser. No. 12/814,181, filed Jun. 11, 2010, which is a continuation-in-part application of, and claims priority to, U.S. application Ser. No. 12/499,841, filed Jul. 9, 2009, which claims priority to U.S. Provisional Patent Application No. 61/079,513, filed Jul. 10, 2008, the entire contents of each of which are incorporated by reference herein.

FIELD OF THE INVENTION

The present invention relates to a method and apparatus for treating vegetation. Specifically, the invention relates to a method and apparatus for the selective killing of plants, or inhibiting plant growth, by inducing extreme hypothermia. The hypothermia is induced by applying a compressed gas, such as carbon dioxide, to selected plants.

BACKGROUND OF THE INVENTION

The presence of undesired plants on a lawn or in a garden can be difficult to treat and frustrating for owners. Removing certain undesired plants while maintaining other plants is a problem on farms, golf courses, and residential yards. Golf course owners may re-sod an entire green or fairway if stubborn summer perennial grasses like some types of Bermudagrass grow on the green or fairway. Re-sodding is a very costly solution for managing the invasion of summer perennial grasses.

Traditional herbicides do not always effectively treat weeds. As more plants are treated with chemical weed killer, plants may develop a tolerance to herbicides, thereby increasing the amount of herbicide required and decreasing efficiency of the treatment. Certain grasses and weeds are difficult to kill and traditional herbicides often require multiple applications before plants die. The use of herbicides may often cause turf to discolor. Also, many herbicides are not intended for use when the temperature reaches 85° F. or warmer. If herbicides are used in warm temperatures, desired grasses often die along with unwanted plants, or the desired grasses may experience extreme stress. As such, traditional herbicides may not effectively remove weeds at the point in the weed growth cycle when weeds grow the most and the quickest without also causing harm to desirable grasses.

Chemical herbicides are harmful to people and the environment. Weed treatments may pose a risk for an individual dispensing weed killer onto a treatment surface since herbicides often contain poisonous chemicals. A chemical residue may remain on a treated area, thereby posing a risk to small children and pets. Harsh chemical weed killers are detrimental to the environment since toxins may leech into the soil and drain into water runoff. Such detrimental effects have prompted increased governmental regulations limiting the type and amount of chemicals utilized to treat weeds and crops.

Accordingly, a need exists for an apparatus and method of vegetation treatment which selectively treats weeds and other undesirable plants while allowing desirable plants to remain.

SUMMARY OF THE INVENTION

In accordance with the present invention, an apparatus is provided to selectively treat undesirable plants. Specifically, the apparatus may be used to deliver a treating substance or material such as compressed gas or liquid to selected summer annual or perennial grasses, and/or to certain summer annual or perennial weeds. The apparatus may include a canister capable of containing a compressed treating substance or material like a compressed liquid or gas. For instance, the canister may contain carbon dioxide or other gases, either alone or as a mixture. The canister may contain traditional or organic herbicides. A dip tube may be provided within the canister for drawing the treating substance from the canister. A length of tubing and/or hose may be provided having a first end and a second end. The first end of the tubing may be connected to the canister. The treating liquid or gas may flow from the canister through the tubing. The second end of tubing may be connected to a nozzle, including any type of spray tip. The nozzle may include an opening through which the treating fluid, such as compressed carbon dioxide gas or liquid, may flow. A valve may be provided along the length of tubing to control the amount and the rate at which the treating liquid and gas is dispensed from the canister. The valve may include a regulator. The valve may be activated by a gear or trigger linkage connecting the valve to a trigger. The gear and trigger may also be connected by a spring that closes the valve when the trigger is released. A delivery mechanism may also be provided. The delivery mechanism may be positioned along the length of tubing and provides for regulating the application of treating material to a selected area.

A method is provided for treating vegetation by inducing hypothermia by applying a hypothermic treating substance or material. For instance, carbon dioxide gas may be applied to selected vegetation to induce hypothermia. Also provided is a method for treating vegetation by applying a treating substance capable of creating a hypothermic response in selected plants. For instance, a substance or material may be applied that is a compressed liquid or gas, or even a solid state. Any gas may be used in connection with the present invention, including inert gas. When compressed gas is utilized, the rapid expansion of the gas causes cooling, and in the case of carbon dioxide, a mixture of carbon dioxide gas and solid carbon dioxide (also known as dry ice) may be dispensed. Depending on conditions, water vapor may also condense as ice or frost on the treated areas. The cold temperature created by this rapid expansion may be utilized to kill undesirable plants or grasses or cause them to become dormant. In a specific application, a method is provided to induce hypothermia by discharging compressed carbon dioxide to one or more summer plants or grasses. The carbon dioxide may be applied for a selected amount of time at a selected pressure. Examples of summer plants that may be killed by hypothermic treatment with carbon dioxide include, but are not limited to, crabgrass, henbit, corn speedwell, seedling white clover, annual bluegrass, chickweed, common dandelion, lespedeza, goosegrass, foxtails, and barnyardgrass. Compressed carbon dioxide may be applied to selected summer grasses to cause the grasses to become dormant. Examples of summer grasses which may become dormant include but are not limited to Bermudagrass, Centipedegrass, St. Augustine grass, Zoysiagrass, and Bahiagrass. The method described herein does not harm cool season grasses such as Fescue, and is unlikely to control perennial white clover, buckhorn plantain, or curly dock. In some embodiments, the application of compressed carbon dioxide gas may cause certain summer grasses to die and certain other summer grasses to become dormant.

The present invention may also be used to treat summer weeds. Carbon dioxide gas may be applied to one or more selected summer weeds for a selected time, pressure, flow rate and/or spray pattern, to kill at least a portion of the weeds. The 
presently claimed invention exploits the relative cold-hardiness of desired plants, such as fescue grass, to allow for the removal of interspersed non-desirable plants, including certain summer grasses such as crabgrass and certain summer weeds such as lespedeza, and to slow or stop the growth of invasive summer perennial grasses such as some types of Bermudagrass. Examples of summer weeds that may be treated include crabgrass, spurge, knotweed, annual bluegrass, chickweed, common dandelion, seedling, white clover, henbit, cord speedwell, and lespedeza.

In some embodiments, the present invention may include the application of adjuvants. Such adjuvants induce the crystallization of water present in the plant. When ice crystallization is sufficient to disrupt the cellular integrity of the vegetation, the result is cell death. An adjuvant of this invention may be any substance used for cloud seeding.

Ice is used to protect frost-susceptible crops like strawberries from subfreezing (e.g., below 32° F.) temperatures by controlling the nucleation of ice crystals. In particular, certain bacteria known to carry ice nucleating proteins, such as *Pseudomonas syringae*, may be applied to induce ice crystallization on the surface of a plant for protection. Alternately, genetically engineered variants of *Pseudomonas syringae* lacking the ice nucleating protein may be introduced to displace the ice-nucleating native bacteria in order to reduce the likelihood of ice crystallization. For this invention, adjuvants may also include certain bacteria known to carry ice nucleating proteins, such as *Pseudomonas syringae*, as well as an ice nucleating protein, for the purpose of inducing ice nucleation within the plant, resulting in the death of all or part of the plant. An adjuvant of this invention can also be silver iodide, *Erwinia herbicola, E. ananas, E. uredovora, Xanthomonas campestris, X campestris pv. translucens, P. fluorescens, P. viridiflava, P. chlororaphis, P. putida, Enterobacter agglomerans, Ent. taylorae, Saccharomyces cerevisiae, Fusarium acuminatu, Fusarium avenaceum*, and *Erwinia ananas*. Other adjuvants of this invention can include but are not limited to, methanol, ethanol, propanol, isopropanol, butanol, and/or isobutanol, as well as any citrus extracts.

The apparatus and methods of the present invention may be utilized in organic gardening and/or organic farming practices, and in conventional farming.

BRIEF DESCRIPTION OF THE DRAWINGS

FIG. 1 is a schematic elevational view of an apparatus for applying compressed carbon dioxide gas to summer grasses and summer weeds in accordance with the present invention.

FIG. 2 shows large crabgrass (2-3 tiller) control seven days after treatment. Fisher's Protected Least Significant Difference (LSD)=5.9.

FIG. 3 shows large crabgrass (3-4 tiller) control seven days after treatment. LSD=5.6.

FIG. 4 shows percent control of 2-3 tiller large crabgrass versus pounds of $CO_2$ applied.

DETAILED DESCRIPTION OF THE INVENTION

In accordance with the present invention, an apparatus 10 for treating plants is provided. As shown in FIG. 1, a canister 20 capable of storing and dispensing a treating substance or material may be provided. The canister 20 may contain treating substances under pressure and/or temperature control such as a compressed gas, compressed liquid, or even a solid. Generally, a compressed treating material or substance within a container is stored in liquid form. The liquid may be stored under a high amount of pressure. Alternatively or in addition, any gas may be used in connection with the present invention, including inert gas. A mixture of gases may be used in connection with the present invention. For example, gases stored with the canister 20 may include carbon dioxide, oxygen, nitrogen, air, or other similar gases. The canister 20 may contain a dip tube 22 to draw the treatment substance such as liquid carbon dioxide from the canister 20 and particularly from the bottom of the canister. The canister 20 may be constructed in a variety of sizes. For instance, the canister 20 may be a smaller size so it may be hand-held or the canister 20 may be a larger size and towed by a vehicle.

The present invention may also provide for a valve 40. The valve 40 may include a regulator. The valve 40 may be connected with the canister 20 or manufactured onto or as a part of the canister. The valve 40 may control the amount and rate of treating substance dispensed from the container 20 and may include an adjustable knob or handle 42 to control the rate of treating substance released from the canister 20. The valve 40 may control the rate of treating substance released from the canister 20 to control the rate of delivery to a selected treatment area. In one embodiment, the valve 40 may be a ball valve or other valve capable of restricting the pressure of the treating substance or gas released from the canister 20. Optionally, a remote trigger capable of actuating the valve 40 may be provided.

The canister 20 may optionally include a release valve to vent the contents of the canister 20. The release valve may include a regulator. Opening the release valve permits gas to flow out of the container from a region of high pressure within the canister 20 to a region of low pressure external to the canister 20. The gas is released quickly from the container to enable the gas to cool upon expansion. Under certain conditions, carbon dioxide that is being released rapidly will form a mixture of solid carbon dioxide (also known as dry ice) and gaseous carbon dioxide. The canister 20 may be positioned so that a release valve is oriented away from the surface to be treated.

A length of dispensing tubing and/or hose 30 having a first end and a second end may be provided. The first end of the tubing 30 may be connected with the canister 20. Specifically, the tubing 30 may be connected with the valve 40, which in turn may be adjacent to or part of the canister 20. In one embodiment of the invention, the tubing is insulated. In certain applications, the canister 20 may contain a liquid having a boiling point lower than the ambient air outside the canister. As the liquid is expelled from the canister 20 it is exposed to the ambient temperature and pressure. The rapid volume or pressure change as the compressed gas enters ambient conditions causes the temperature to drop ($PV=nRT$). The discharge of the canister 20 happens too quickly for thermal equilibrium to be established. Depending on conditions, either gas or a mixture of gas and solid carbon dioxide may be dispensed. The present invention utilizes this non-adiabatic expansion to impart hypothermic damage to the targeted plant. The tubing 30 may include or be connected with a dispensing nozzle, for example, in the form of an output dispensing nozzle tube 88 located along or at the distal portion of the tubing 30 and having a nozzle so mounted or manufactured or a free end of the nozzle tube 88 thereby providing, for example, a spray wand.

The tubing 30, as well as dispensing nozzle tube 88, may be rigid or flexible and must have an appropriate pressure rating. For increased efficiency and protection of the user, the tubing 30, as well as nozzle tube 88, may be insulated. If the temperature of the treating substance increases while in the tubing 30 or 88, the resultant pressure increase may exceed the design specifications of some types of tubing. Therefore, tubing 30 and 88 should be made from appropriate materials. Nonlimiting examples of tubing include ¼" stainless steel tubing and ¼' braided stainless steel tubing.

The nozzle 50 may be positioned directly at the second end of the length of tubing 30 or may be connected by additional tubing, such as the nozzle tubing 88. Specifically, the nozzle 50 may be positioned along the output nozzle tube 88. The nozzle 50 may cooperate with the valve 40 for dispensing treating substance to a selected area. In one embodiment, the treating substance may be dispensed through the nozzle 50 to selectively treat one or more undesirable plants which may include weeds, grasses, summer annual grasses, and/or summer annual plants. Compressed gas or liquid stored within the container 20 may flow through the tubing 30 and is released into the ambient environment through nozzle 50. The nozzle 50 may include any type of spray tip, such as a spray nozzle, a high velocity nozzle, a length of capillary tubing, or other similar nozzle. The nozzle 50 may contain a needle or capillary tube through which the treating substance may exit the apparatus 10. For instance, once compressed gas leaves the nozzle 50, the released gas will expand rapidly. The size of the opening of the nozzle 50 and/or needle may be selected based upon the type of treating substance such as gas, size of canister 20, and length of tubing 30 used as well as storage pressures and temperatures. The nozzle 50 may have a small opening, for example, a zero degree nozzle.

The nozzle 50 may be enclosed in an insulated cone or box, 52, to direct the application of the gas and to insulate the hypothermic microenvironment. The use of an insulated cone 52 may increase the efficiency of the treatment by one or more orders of magnitude. Increasing the efficiency means that the $LD_{50}$ (lethal dose to 50% of plants) is decreased from 2 pounds of $CO_2$ per plant to less than 0.2 lbs/$CO_2$ per plant. The insulated box or cone may be made of layers of materials comprising or consisting of plastic, insulating foam, and/or metal.

A delivery control mechanism 80 may be provided to selectively dispense a treating substance from the canister 20. The delivery mechanism 80 may be positioned along the length of tubing 30 between the canister 20 and the nozzle 50. Specifically, the delivery mechanism 80 may be positioned between the canister and the output tubing 88. The nozzle 50 may be positioned at the distal end of the output tube 88. The delivery mechanism 80 may include a handle 82 for ease of use. The delivery mechanism 80 may include a delivery valve 84 to control the rate at which the treating substance is dispensed from the canister 20 through the nozzle 50. The delivery valve 84 may include a regulator. The delivery mechanism 80 may also include a trigger, grip activator, or other actuation mechanism 86. Activating the trigger 86 may cause a select amount of treating substance to be released from the canister 20. Specifically, activation of the trigger 86 may actuate a trigger linkage 90, which in turn actuates the delivery valve 84. Optionally, a spring is provided to close the delivery valve 84 upon release of the trigger 86. In one embodiment, the delivery valve 84 may include a ball valve capable of regulating the amount of treating substance released. Upon squeezing the trigger 86, the treating substance may be discharged from the canister 20 through the output tube 88 and the nozzle 50 at the end of the output tube 88 to spray a selected area. In one embodiment, a remote trigger capable of actuating the delivery valve 84 is provided. The output tube 88 may be configured to apply gas or treating fluid at a selected distance from plants. In one embodiment, the output tube 88 may apply gas to ground level. In one embodiment, a delivery mechanism 80 including a trigger 86 and output tube 88 may be provided to facilitate short burst spraying.

A vapor canister 60 may be provided to increase the amount of water vapor in the ambient air. The vapor canister 60 may include a vapor sensor or humidity detector 62 to alert the user when the moisture content of the surroundings is low or at, below, or above a selected level. The vapor canister 60 may be attached beside the canister 20 of compressed gas or the vapor canister 60 may be separate from the canister 20. For example, the efficacy of the compressed gas to destroy plants may be improved if the ambient air is moist. Accordingly, a vapor canister 60 may be used to supplement the dry air, thereby increasing the effectiveness of the compressed gas to treat plants. Locations where the use of a vapor canister 60 may be desirable include desert environments.

A transporter 70 may be used to transport the canister 20 to desired locations or during treatment. The transporter 70 may include a cart or trolley having one or more sets of wheels so that a user may move the canister 20 to or at a desired location. The wheels may be large spoke wheels, pneumatic tires, or other similar wheels.

The present invention may have a plurality of configurations. The present invention may be used as a small hand-held aerosol container to spray weeds for private or residential use. One benefit of a small sized container is that the container may be recycled or more easily transported.

The apparatus 10 may be larger so that a larger area of land can be treated. For instance, the canister 20 may hold at least five pounds of compressed gas or treating substance. Tubing 30 for use in conjunction with a five pound canister 20 may be thick and durable hose or tubing. Examples of suitable hose include high pressure hoses used on trucks and heavy equipment, stainless steel braided hoses, and stainless steel tubing. Optionally, one or more shoulder straps may be provided to facilitate ease of use of the apparatus 10 by an individual. In one example, the canister 20 may be made available to consumers with the shoulder strap and transporter. The canister 20 may be recycled and/or refillable.

Even larger canisters 20 may be utilized. For instance, canisters 20 may be configured to hold five, ten, fifteen, twenty, twenty five, or thirty pounds (e.g., 5, 6, 7, 8, 9, 10, 11, 12, 13, 14, 15, 16, 17, 18, 19, 20, 21, 22, 23, 24, 25, 26, 27, 28, 29, 30), or even more, of compressed gas or treating substance. Larger canisters, for instance such as ten pound containers or even larger, may treat an area of one hundred to five hundred square feet or larger, or may be used to spot-treat over an even larger area. The containers may be purchased along with a suitable transporter 70.

Larger commercial applications may also be provided. In lieu of portable canisters 20, tanks may be utilized. Tanks may accommodate fifty or more pounds of compressed gas. Large tanks may exceed fifty pounds but an operator should be able to appropriately position the tank or at least the spray nozzle or nozzles to treat a desired section of land. The tank, a suitable delivery mechanism and a suitable transporter may be positioned on a unit towed behind the operator. For instance, a small boom may be used to dispense the treating fluid so that the operator may cover a greater amount of land. The boom unit may dispense compressed gas to one or more residential yards. A large tank for extended spraying may also be provided on a tow trailer behind the tank. For instance, the tow trailer might be attached to a vehicle such as a truck. The operator may ride the apparatus while simultaneously spraying a selected area. The tank may be mounted directly onto a vehicle. The vehicle may have several hundred feet of hose and the hose could be pulled across a yard to spray a particular spot. A hose reel may be employed to store the tubing. Larger, towable tanks may be utilized in agricultural settings to treat larger tracts of land. Providing insulating cones, boxes, or 
other semi-enclosed insulation will improve the efficiency of application on any scale. Further, the compressed gas may be nebulized or atomized as it is applied to a selected area.

The present invention includes a method to treat certain vegetation such as selected grasses or weeds to either kill selected vegetation or to induce dormancy in certain vegetation. The susceptibility of plants to cold may be harnessed to selectively determine which plants survive. One or more treating substances, for instance, compressed gases are sprayed onto a plant, thereby stunting plant growth. Optionally, the treating substance may include a gaseous carrier of an herbicide. In one embodiment, the treating substance may include compressed carbon dioxide. Other gases that may be applied for treating plants include air, nitrogen, oxygen or any mixture of gases and such gas or gas mixture may be selected to treat different plants or to match temperature or gas properties of the gas or gas mixture to different plants. Application of compressed gas, such as carbon dioxide, may kill plants which are not resistant to cold temperatures. Those plants that are resistant to cold temperatures survive the hypothermic treatment.

Different types of plants may be treated with the present invention. In general, plants that become dormant during colder weather may be referred to as "perennial," while plants that regenerate from seed after a cold season are called "annuals." Annuals typically only grow during warm months. Accordingly, annual plants may be referred to as "warm season plants" whereas perennial plants may be referred to as "cool season plants."

Ground temperature may influence plant growth to a greater extent than air temperature. For example, ground temperatures may drop to as low as −40° F. or even −60° F. and grasses or plant life adapted to cold temperatures can survive. Above-ground parts of plants may die while the roots remain viable under the soil. If the roots remain at an appropriate temperature, the plant will survive cold temperatures. Summer annual weeds and grasses are usually killed off in the first autumn frost and are very susceptible to cold temperatures. Accordingly, summer annual grasses and weeds are particularly vulnerable to hypothermic treatment with compressed gas. In general, summer annual plants, including weeds and grasses, die when treated with compressed gas, while summer perennial grasses become dormant. One such example of a summer perennial grass that becomes dormant in colder temperatures includes some types of Bermudagrass. Alternatively or in addition, summer annual plants, such as grasses or weeds, may be harmed from hypothermic treatment. Application of treating substance may eradicate one or more plant species that encroach upon an area, particularly in tropical or subtropical climates. The use of hypothermic treatment may be utilized in connection with organic farming and/or organic gardening.

The ability to selectively kill at least a portion of certain plants while other plants remain unharmed is highly desirable. The present invention provides a method to inhibit plant growth by applying a treating substance, including for instance compressed carbon dioxide gas, to a plant surface. Release of compressed gas from a canister 20 causes a decrease in temperature near a selected plant surface. Water vapor may freeze and be deposited on the plant surface, thereby frosting the plant. In one embodiment, the compressed gas may cause ambient air to reach a temperature of as low as −40° F. For example, the compressed gas can be used to drop the temperature of ambient air to a temperature within −40° F. and 32° F. As an additional example, the use of carbon dioxide and/or dry ice may cause ambient air temperature to drop to approximately −109° F. and some plants may survive after being exposed to such low temperature. Plants resistant to colder temperatures survive, while plants susceptible to cold temperatures may be killed or become dormant.

Grasses may include plants that flourish during warm weather months but die or become dormant in cooler weather months. Examples of summer annual grasses which may be treated include but are not limited to crabgrasses (*Digitaria* spp.), goosegrass (*Eleusine indica*), foxtails (*Setaria* spp.), and barnyardgrass (*Echinochloa crusgalli*). Summer perennial grasses which become dormant in cooler weather months include but are not limited to some types of Bermudagrass, Centipedegrass, St. Augustine grass, Zoysiagrass, and Bahiagrass.

In some embodiments of this invention, a method is provided for treating summer weeds. A weed may include an undesirable plant. A weed may also include a plant that grows in an undesirable location. Summer weeds are plants that grow during warm weather months and die or become dormant in cooler weather. Examples of summer annual weeds which may be treated include but are not limited to Spurge, knotweed, and lespedeza.

The rate, volume, and/or moisture content of treating substance dispensed from the container may be regulated. Treating substance within the container is dispensed over a selected length of time. In certain instances, application of short bursts of treating substance may be desirable; in other instances, it may be desirable to provide a continuous application of treating substance to one or more selected targets.

In some embodiments, the present invention provides an apparatus for inducing hypothermia in a plant, comprising: a canister for containing a hypothermia-inducing substance; a valve cooperating with the canister for controlling the amount of the hypothermia-inducing substance dispensed from the canister; and a nozzle cooperating with the valve for dispensing the hypothermia-inducing substance from the canister onto the plant to induce hypothermia in the plant. In the apparatus of this invention, the canister can include a dip tube, a remote trigger, wherein the remote trigger actuates the valve and/or a spray tip on the nozzle, in any combination. The apparatus can also include a nozzle that is enclosed in an insulating cone, insulating container, insulating vessel or insulating structure.

In particular embodiments, the apparatus of this invention can be adapted to dispense the hypothermia-inducing substance in a metered dose. Dispensing of the substance in a metered does would be accomplished by using a microcontroller to cause the valve to operate in a preprogrammed manner, for example to be open for a fixed amount of time, or for example to be opened for iterative time exposures. In another embodiment, the apparatus can be adapted to notify the operator of the preprogrammed dispensing by showing different colored lights (e.g., red and green). The apparatus can have a dose counter to display how many doses have been dispensed and/or how many doses are remaining. In further embodiments, the apparatus of this invention can be adapted to contain a compressed gas (e.g., a gas held under pressure at or above 600 psi). In a specific embodiment, the compressed gas can be compressed carbon dioxide gas.

In embodiments in which the apparatus of this invention has a nozzle that is enclosed in an insulating cone or other insulating container or vessel or structure, carbon dioxide gas can be dispensed at a dose range from about 0.05 lb/square foot to about 0.2 lb/square foot. In particular embodiments, the carbon dioxide gas can be dispensed at a dose of about 0.15 lb/square foot.

Furthermore, embodiments of the apparatus of this invention include an apparatus comprising a radio frequency identification (RFID) tag operably associating the nozzle and the canister.

The present invention also provides methods, which can employ the apparatus of this invention as well as any other apparatus suitable for carrying out the methods described herein. Thus, in one embodiment the present invention provides a method for inducing hypothermia in one or more plants, comprising applying a hypothermia-inducing substance that is contained under pressure to the one or more plants at a selected flow rate for a selected amount of time to induce hypothermia effective to kill at least a portion of the one or more plants. In various embodiments, the hypothermia-inducing substance can be compressed carbon dioxide gas. A range of flow rates for the methods of this invention is from about 0.25 lbs/minute to about 10 lbs/minute and in some embodiments the flow rate can be from about 0.5 lbs/minute to about 4.0 lbs/minute. A range of application times for the methods of this invention is from about 0.5 seconds to about 2 minutes.

Also provided herein is a method for inducing hypothermia in undesirable plants in a population of plants comprising desirable and undesirable plants, comprising applying a hypothermia-inducing substance that is contained under pressure to the population of plants at a selected flow rate for a selected amount of time to induce hypothermia effective to kill at least a portion of the undesirable plants in the population.

The methods of this invention can be employed to induce hypothermia in, e.g., summer annual plants. Nonlimiting examples of summer annual plants include grasses, weeds, invasive plant species and any combination thereof. Additional nonlimiting examples of a plant of this invention include crabgrass, annual bluegrass, seedling white clover, henbit, corn speedwell, common chickweed, common dandelion, goosegrass, foxtails, barnyardgrass, spurge, knotweed, lespedeza, a herbicide resistant plant, a glyphosate resistant plant (e.g., Palmer amaranth or pigweed) and any combination thereof. In particular embodiments, the plant is crabgrass.

The methods of this invention can further comprise the step of applying an herbicide to the one or more plants or to the population of plants. Nonlimiting examples of herbicides of this invention include glyphosate (also known as RoundUp), which is a nonselective herbicide, as well as Drive 75, Acclaim, Speedzone and Target, which are selective herbicides.

In further embodiments, the methods of this invention can comprise the step of applying an ice nucleation-inducing substance that results in ice nucleation in the one or more plants or in the undesirable plants in the population of plants. Nonlimiting examples of the ice nucleation-inducing substance of this invention include silver iodide, an ice nucleating bacterium (e.g., *Pseudomonas. syringae*), an ice nucleating protein and any combination thereof.

In methods employing the application of an herbicide or an ice nucleation inducing substance, these can be applied before, after and/or simultaneously with the application of the hypothermia-inducing substance. In some embodiments, both an herbicide and an ice nucleation-inducing substance can be applied before, after and/or simultaneously with the application of the hypothermia-inducing substance. In some embodiments the herbicide and/or ice nucleation inducing substance, if soluble, can be dissolved in the hypothermia inducing substance (e.g., carbon dioxide). Thus, in various embodiments, the hypothermia-inducing substance, the herbicide and the ice nucleation-inducing substance can be applied from the same apparatus (e.g., combined in the canister or from separate canisters) or applied from separate apparatuses.

In the methods of this invention, the application of the hypothermia-inducing substance can result in frost on the one or more plants.

In the methods of this invention, the one or more plants to be targeted for hypothermia can be present among row crops (e.g., corn, soy beans, cotton). Thus, the methods of this invention can be carried out in a conventional farming or organic farming environment.

In particular embodiments of this invention, a method is provided, of killing all or part of a plant, comprising applying to the plant carbon dioxide gas under pressure from an apparatus comprising: a canister for containing the carbon dioxide gas, a valve cooperating with the canister for controlling the amount of the carbon dioxide gas dispensed from the canister; and a nozzle cooperating with the valve; said nozzle being enclosed in an insulating cone wherein the carbon dioxide gas is applied at a flow rate and for a period of time effective to kill all or part of the plant. Such a method can further comprise applying an adjuvant to the plant, which can be silver iodide, an ice-nucleating bacterium (e.g., *Pseudomonas syringae*), an ice-nucleating protein and any combination thereof. In such a method the plant to be killed, all or in part, can be crabgrass.

As used herein, "a," "an" or "the" can mean one or more than one. For example, "a" cell can mean a single cell or a multiplicity of cells. Also as used herein, "and/or" refers to and encompasses any and all possible combinations of one or more of the associated listed items, as well as the lack of combinations when interpreted in the alternative ("or"). Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

EXAMPLES

Example 1

One application of compressed air may be sufficient to stunt or kill certain summer annual grasses and certain summer annual weeds. During one informal experiment, application of compressed air to a patch of crabgrass approximately 1 square foot in size slowed plant growth as soon as 24 hours after treatment. After a period of 48 hours the crabgrass had started to discolor. After 72 hours most of the crabgrass had disappeared while the surrounding Tall Fescue, a cool season grass, remained unchanged. Similar experimental results have been obtained when compressed gas is applied to other unwanted plants in the presence of Fescue. Compressed air applied to Bermudagrass slowed growth after a period of 24 hours. The Bermudagrass appeared dormant after 48 hours. After 72 hours the grass appeared completely dormant. The Bermudagrass did not show signs of re-growth for a period of approximately five days after the initial application of compressed air during extremely hot, humid summer conditions (over 95° F. and 100% humidity).

Example 2

Greenhouse-grown crabgrass plants were treated with the prototype containing either an 8002 flat fan nozzle (which was measured to release 2 pounds of $CO_2$ per minute) or with an 8004 flat fan nozzle (which releases 4 pounds of $CO_2$ per minute), to determine if the rate of application affects the percent control achieved. Control means killing or death of the plants as determined by visual observation. The percent control is a visual rating of the treated plant compared to an untreated control plant. In other words, it is the percent of plant death. Trials were conducted in triplicate.

Figure 1:
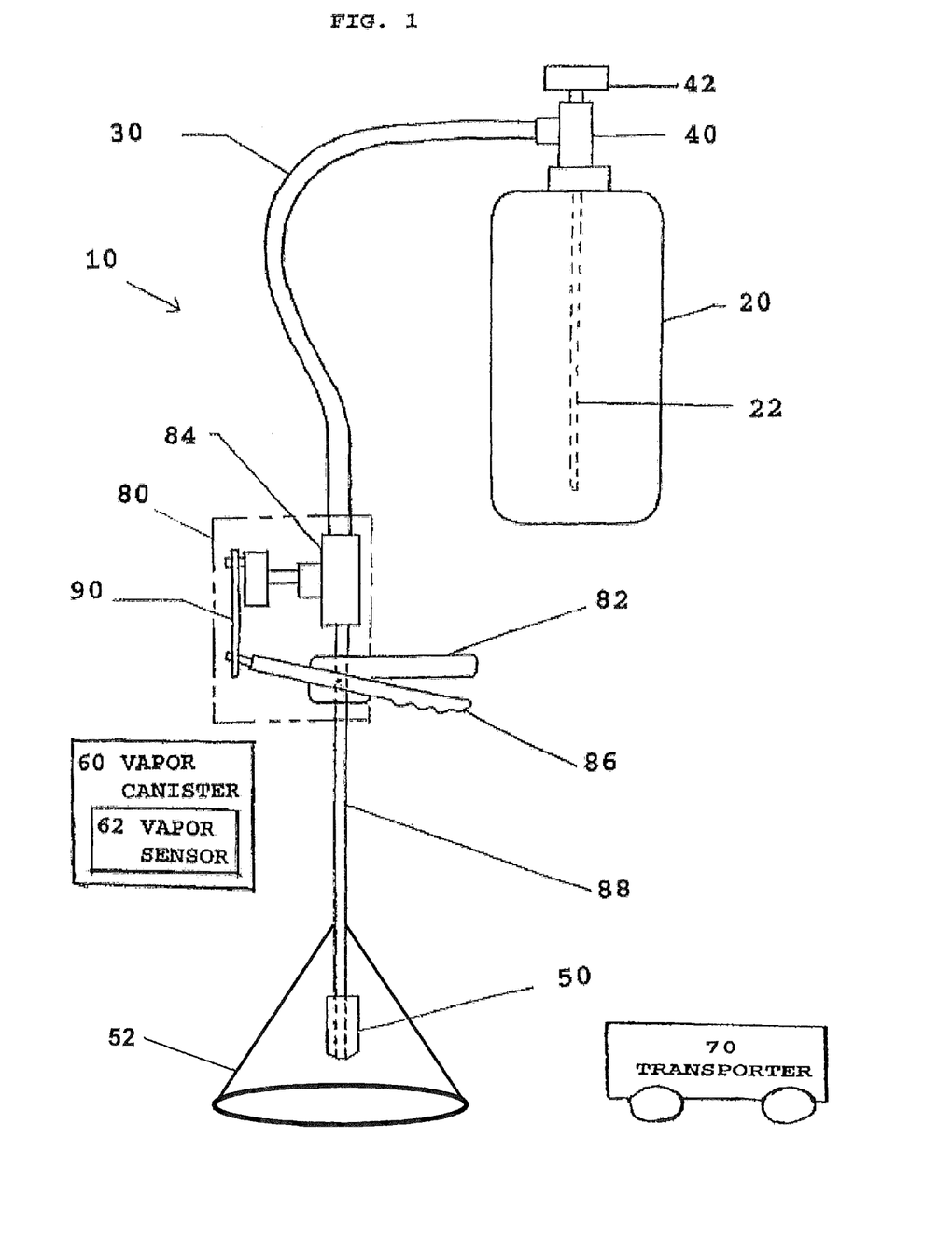
Figure 2:
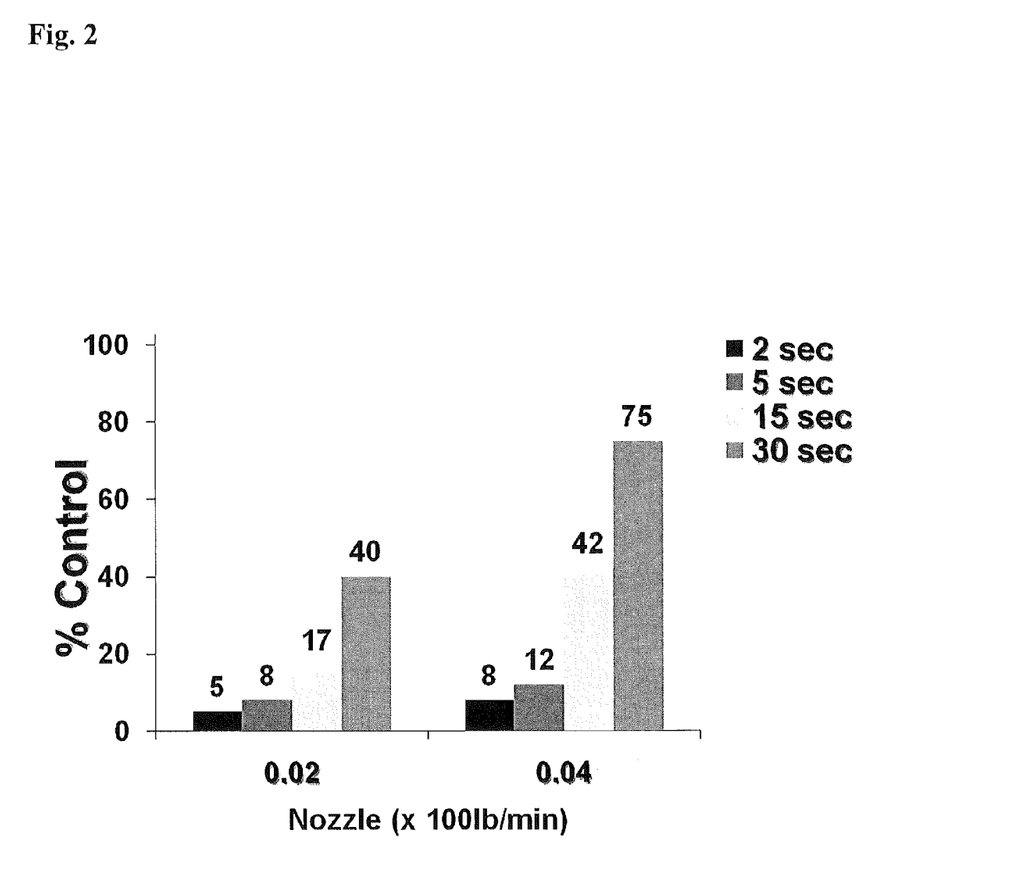
Figure 4:
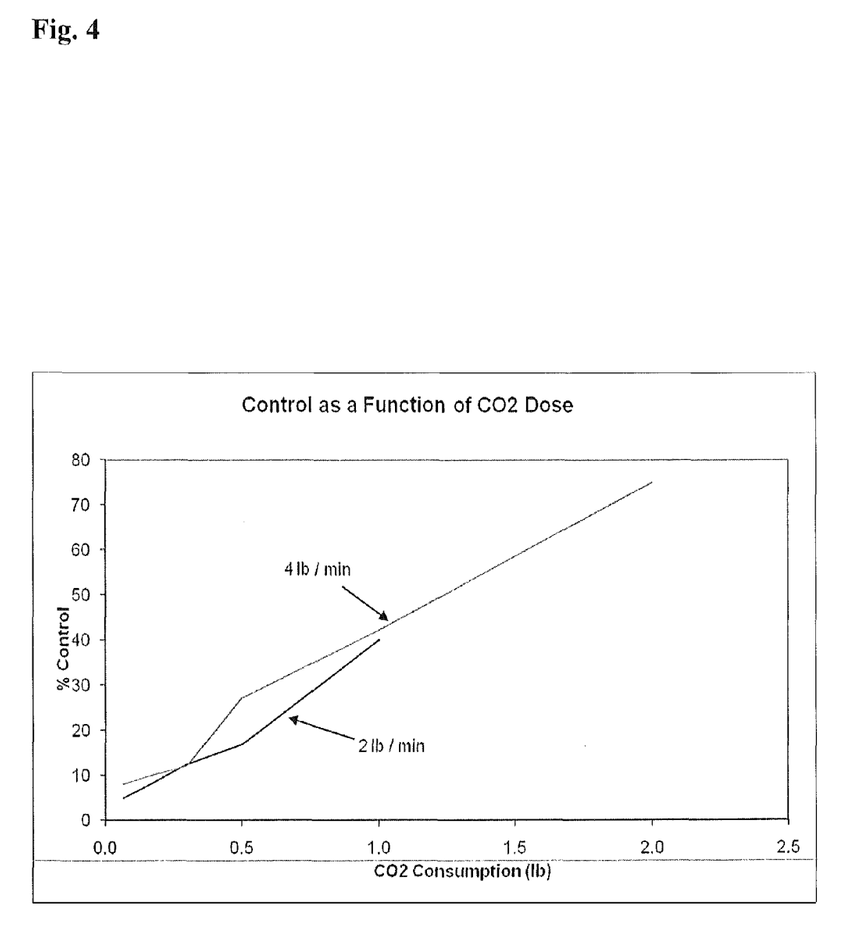

As shown in FIG. 2, treatment for 30 seconds with the 2 lb/min nozzle results in 40 percent control, while treatment with the 4 lb/min nozzle for 15 seconds results in 42 percent control; in both cases one pound of $CO_2$ was dispensed. Similarly, treatment for 15 seconds with the 2 lb/min nozzle results in 17 percent control with 0.5 pounds of $CO_2$ dispensed, while treatment with the 4 lb/min nozzle for 5 seconds results in 12 percent control with 0.3 pounds of $CO_2$ dispensed. From this study, it was concluded that for crabgrass, the total amount (dose) of $CO_2$ applied correlates with % control. See FIG. 4, which graphs % control vs. $CO_2$ dose with two different application rates.

Figure 3:
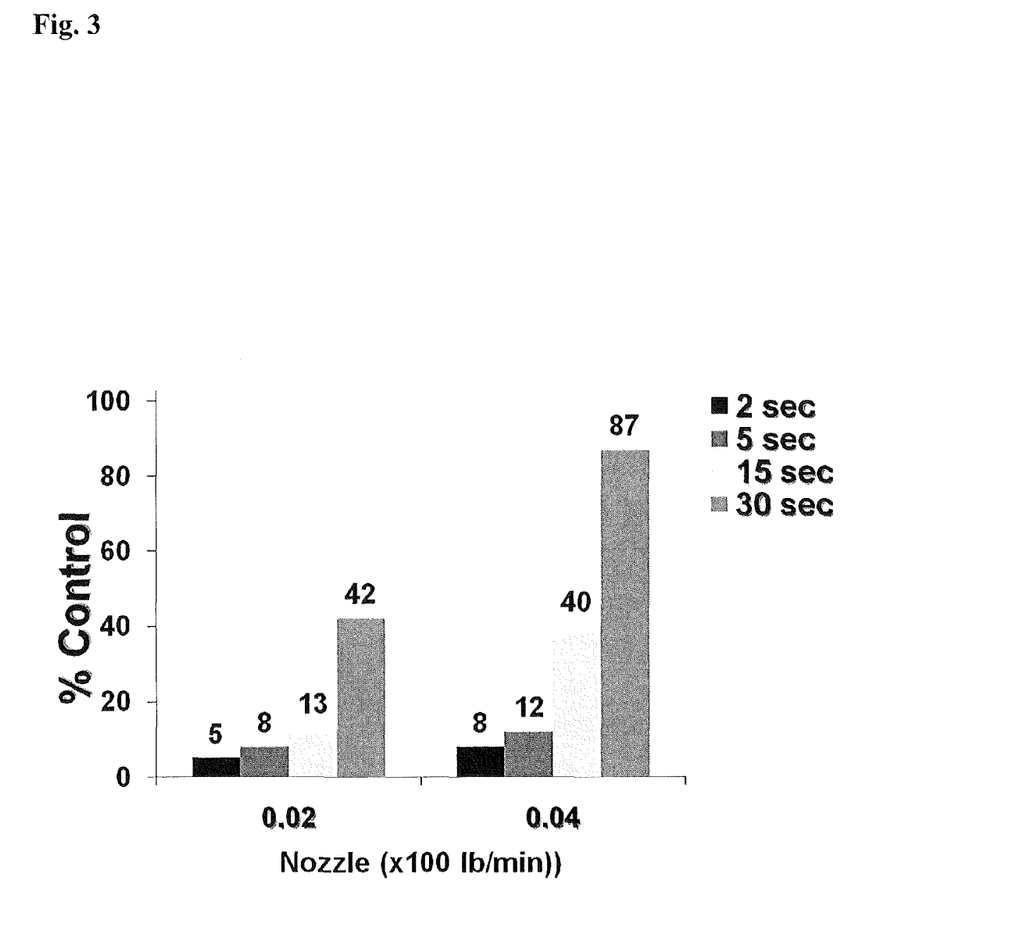

In the data presented in FIG. 3, the crabgrass plants are larger. They are at the 3-4 tiller stage, whereas the plants in the data presented in FIG. 2 were 2-3 tiller plants. The $CO_2$ application controlled both plant sizes well, and with the larger plants the same trend of percent control corresponding to the total pounds of $CO_2$ applied was observed. In both cases the $LD_{50}$ is over 1 pound $CO_2$/plant.

Most commercial herbicides achieve 80% control or better. The prototype used 2 pounds of $CO_2$ to achieve this level of control for one 6" plant. At the 2 lb/plant dispensing rate, a commercial 25-lb cylinder of $CO_2$ would only treat 10 plants; clearly efficiency increases were needed to create a viable backpack sprayer system. An insulating cone was attached around the nozzle with the expectation of possibly achieving a modest increase in efficiency, perhaps cutting the $CO_2$ requirement by 20-50%.

Quite surprisingly, upon addition of this insulating cone, it was possible to achieve 80% control or better by spraying only 0.15 lbs of carbon dioxide on field-grown 2-3 and 3-4 tiller plants. These results were repeated with a 1-lb/min nozzle sprayed for 9 seconds and a 3-lb/min nozzle sprayed for 3 seconds. Unexpectedly, a greater than ten-fold reduction in the $CO_2$ usage was achieved (Table 1). The results are especially remarkable since field-grown plants (treated with the insulated design) are usually harder to kill than greenhouse-grown plants that were treated with the non-insulated design.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

TABLE 1

Control with the initial non-insulated prototype and the modified insulated prototype designs

| stage | % control | non-insulated (lbs $CO_2$) | Insulated (lbs $CO_2$) |
| --- | --- | --- | --- |
| 2-3 tiller greenhouse | 75 | 2 | |
| 3-4 tiller greenhouse | 87 | 2 | |
| 2-3 tiller field | 80+ | | 0.15 |
| 3-4 tiller field | 80+ | | 0.15 |

What is claimed is:

1. A method of selectively killing all or part of an undesirable plant or inducing dormancy in an undesirable plant in a population of plants comprising desirable and undesirable plants, comprising applying carbon dioxide to the population of plants in an amount effective to selectively kill all or part of an undesirable plant or induce dormancy in an undesirable plant in the population of plants comprising desirable and undesirable plants.

2. The method of claim 1, wherein the undesirable plant is an annual plant.

3. The method of claim 2, wherein the annual plant is a plant selected from the group consisting of grass, crabgrass, weed, an invasive plant species, goosegrass, foxtails, barnyard grass, spurge, knotweed, lespedeza and any combination thereof.

4. The method of claim 1, wherein the undesirable plant is selected from the group consisting of Bermudagrass, Centipedegrass, St. Augustine grass, Zoyziagrass, Bahiagrass and any combination thereof.

* * * * *